(12) United States Patent
Cassone

(10) Patent No.: US 7,407,488 B2
(45) Date of Patent: *Aug. 5, 2008

(54) METHOD FOR TREATING CERTAIN BLOOD-MANIFESTED MEDICAL DISORDERS WITH ACOUSTIC WAVES

(76) Inventor: Alphonse Cassone, 4171 Moorecroft St., Las Vegas, NV (US) 89147

( * ) Notice: Subject to any disclaimer, the term of this patent is extended or adjusted under 35 U.S.C. 154(b) by 1226 days.

This patent is subject to a terminal disclaimer.

(21) Appl. No.: 10/166,749

(22) Filed: Jun. 12, 2002

(65) Prior Publication Data

US 2002/0151828 A1    Oct. 17, 2002

Related U.S. Application Data

(63) Continuation-in-part of application No. 09/619,358, filed on Jul. 19, 2000, now Pat. No. 6,500,134, and a continuation-in-part of application No. 09/619,357, filed on Jul. 19, 2000, now Pat. No. 7,077,815.

(51) Int. Cl.
*A61H 23/00* (2006.01)
(52) U.S. Cl. .......................................... 601/47; 601/55
(58) Field of Classification Search .................. 601/46, 601/47, 48, 49, 55, 56
See application file for complete search history.

(56) References Cited

U.S. PATENT DOCUMENTS

| | | | | |
|---|---|---|---|---|
| 3,585,991 A | * | 6/1971 | Balamuth | 601/157 |
| 5,097,821 A | * | 3/1992 | Eakin | 601/47 |
| 5,695,455 A | * | 12/1997 | Alton et al. | 601/47 |

FOREIGN PATENT DOCUMENTS

| | | | |
|---|---|---|---|
| EP | 465870 A1 | * | 1/1992 |
| EP | 891761 A2 | * | 1/1999 |
| WO | WO 9827923 A1 | * | 7/1998 |

* cited by examiner

*Primary Examiner*—Danton DeMille
(74) *Attorney, Agent, or Firm*—Jeffrey Weiss; Janine Rickman Novatt; Weiss & Moy, P.C.

(57) ABSTRACT

A method for treating medical disorders manifesting themselves in the blood, including diabetes and anemia, by exposing the sufferer to audible acoustic waves from a transducer immersed in liquid. The person is preferably placed between one and twenty feet from the wave source, and is preferably exposed to waves at a frequency of about 600 Hertz for approximately twenty five minutes. In one embodiment, the person sits in a jacuzzi-like container together with the transducer.

13 Claims, 1 Drawing Sheet

METHOD FOR TREATING CERTAIN BLOOD-MANIFESTED MEDICAL DISORDERS WITH ACOUSTIC WAVES

CROSS-REFERENCE TO RELATED APPLICATION

This is a continuation-in-part of each of U.S. patent application Ser. No. 09/619,358, filed Jul. 19, 2000 now U.S. Pat. No. 6,500,134, in the name of the Applicant, to which priority is claimed and U.S. patent application Ser. No. 09/619,357, filed Jul. 19, 2000 now U.S. Pat. No. 7,077,815, also in the name of the Applicant, to which priority is claimed.

FIELD OF THE INVENTION

This invention relates generally to methods for treating medical disorders and, more specifically, to a method for treating medical disorders manifested in the blood through the use of acoustic waves.

BACKGROUND OF THE INVENTION

In U.S. patent application Ser. Nos. 09/619,358 and 09/619,357, of which this application is a continuation in part, Applicant disclosed the use of acoustic waves to treat circulatory disorders and body tissue disease. The present application is directed to the use of acoustic waves to treat certain other medical disorders, including specifically diabetes and anemia, that are manifested in the blood.

Both diabetes and anemia produce an abnormal blood condition. The term diabetes mellitus refers generally to a group of disorders that lead to an elevation of glucose in the blood. The two major types of diabetes mellitus are type I diabetes and type II diabetes. Type I diabetes commonly develops in people younger than age 20, and is therefore sometimes known as juvenile diabetes. In type I diabetes, there is an absolute deficiency of insulin, which is needed to aid the entry of glucose into body cells. Regular injections of insulin are required to prevent death.

Type II diabetes is far more common than type I, and represents about 90% of all diabetes cases. Sometimes referred to as adult onset diabetes, it occurs most often in people who are over the age of 40 and are overweight. Unlike with type I diabetes, the high glucose levels in the blood of a person suffering from type II diabetes can usually be controlled by diet, exercise, and weight loss—though sometimes use of an antidiabetic drug is needed. In some cases, insulin injections are required.

Diabetes can lead to a number of different complications. These include blindness due to diabetic retinopathy (each year in the United States, 12,000 to 24,000 people lose their sight because of diabetes); kidney disease due to diabetic nephropathy (10 to 21% of all people with diabetes develop kidney disease, sometimes requiring dialysis or a kidney transplant); heart disease and stroke (diabetes sufferers are 2 to 4 times more likely to have heart disease or to suffer a stroke); nerve disease and amputations (about 60-70% of people with diabetes have mild to severe forms of diabetic nerve damage, which can lead to the need for lower limb amputations); and impotence (affecting approximately 13% of men with type I diabetes and 8% of men with type II diabetes).

Anemia generally refers to a condition in which the oxygen-carrying capacity of the blood is reduced, and is characterized either by reduced numbers of red blood cells or a decreased amount of hemoglobin in the blood. Anemia leads to fatigue and intolerance to cold. There are a number of different kinds of anemia, including iron-deficiency anemia, pernicious anemia, hemorrhagic anemia, hemolytic anemia, aplastic anemia, and sickle-cell anemia. Iron-deficiency anemia is the most common, and is caused by inadequate absorption of excessive loss of iron. Women are the most frequent sufferers from iron-deficiency anemia.

Anemia treatments depend on the kind of anemia from which the patient suffers, and range from the use of iron supplements to blood transfusions, and even to bone marrow transplants.

It should be clear then that each of these disorders presents a problem to those who are afflicted, and that safe and effective treatments are desirable. With respect to treatment methods, non-invasive, non-surgical techniques are generally preferred to surgery. Moreover, safe non-chemical treatments are generally preferred to the use of medications, which can have foreseen or unforeseen side-effects on the body. The present invention is directed to a treatment for each of these disorders—a treatment that is non-invasive, non-surgical, and non-chemical.

In U.S. Pat. No. 5,132,942, issued to applicant herein, a low frequency electroacoustic transducer (the "Cassone Transducer") is disclosed. According to U.S. Pat. No. 5,132,942, the Cassone Transducer could be used to efficiently disperse emulsions, chemical and other wastes, and the like for recycling and environmental enhancement. The Patent does not disclose the use of the Cassone Transducer for medical purposes. It is to that use that the current invention is directed.

SUMMARY OF THE INVENTION

It is an object of this invention to provide a non-invasive method for treating certain medical disorders manifested in the blood, including diabetes and anemia.

It is a further object of this invention to provide a non-surgical method for treating certain medical disorders manifested in the blood, including diabetes and anemia.

It is a still further object of this invention to provide a non-chemical method for treating certain medical disorders manifested in the blood, including diabetes and anemia.

It is a still further object of this invention to provide a method for treating certain medical disorders manifested in the blood, including diabetes and anemia, through the use of acoustic waves.

BRIEF DESCRIPTION OF THE PREFERRED EMBODIMENTS

In accordance with one embodiment of the present invention, a method for treating medical disorders manifested in the blood is disclosed. The method comprises the steps of: providing a low frequency sonic transducer; immersing the low frequency sonic transducer in a liquid-containing container; positioning a person having a medical disorder manifesting itself in the blood a therapeutically beneficial distance from the container; wherein the therapeutically beneficial distance is between approximately one foot and approximately twenty feet from the container; and exposing the person for a therapeutically beneficial period of time to acoustic waves from the low frequency sonic transducer at a therapeutically beneficial frequency.

In accordance with another embodiment of the present invention, a method for treating medical disorders manifested in the blood is disclosed. The method comprises the steps of: providing a low frequency sonic transducer; immersing the low frequency sonic transducer in a liquid-containing container; positioning a person having a circulatory disorder between approximately one foot and approximately twenty feet from the container; and exposing the person for between approximately fifteen minutes and forty-five minutes to acoustic waves from the low frequency sonic transducer at approximately six hundred Hertz.

In accordance with still another embodiment of the present invention, a method for treating medical disorders manifested in the blood is disclosed. The method comprises the steps of: providing a low frequency sonic transducer; immersing the low frequency sonic transducer in a liquid-containing container; positioning at least a portion of a body a person having a medical disorder manifesting itself in the blood in the liquid-containing container; and exposing the person for between approximately fifteen minutes and forty-five minutes to acoustic waves from the low frequency sonic transducer at approximately six hundred Hertz.

DETAILED DESCRIPTION OF THE PREFERRED EMBODIMENTS

The present invention is concerned with an improved method for treating certain medical disorders manifesting themselves in the blood. Such disorders include but are not limited to diabetes and anemia.

Figure 2:
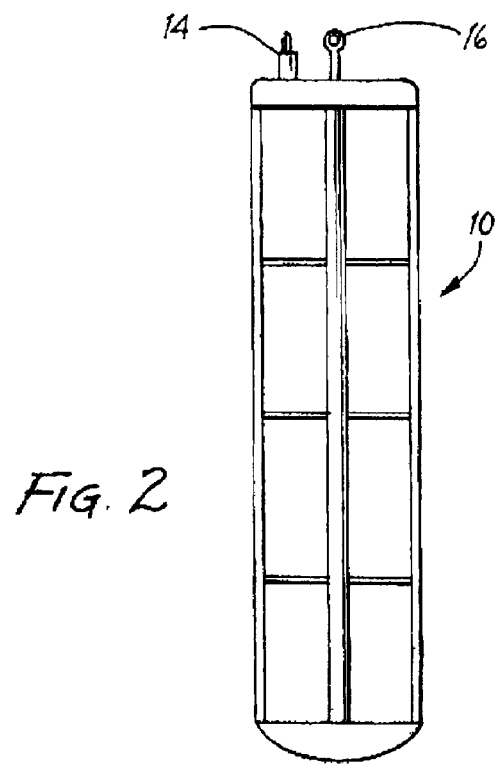
FIG. 2 is a side, cross-sectional view of an electroacoustic transducer of the type preferably used in the method of the present invention.

The method begins with the placement of a transducer 10 like the Cassone Transducer in a container 12 containing water or another liquid. The container 12 preferably has a volume ranging from one to five hundred gallons, with a volume of between five and fifty five gallons regarded as particularly preferred and a volume of approximately fifty gallons regarded as optimal. Preferably, the transducer 10 is modified slightly from the Cassone Transducer shown in U.S. Pat. No. 5,132,942 by the addition of a water-tight electrical connector 14 to replace the coaxial supply line and terminal 10 shown in FIG. 2 of U.S. Pat. No. 5,132,942, and an eye-bolt 16 to replace the pair of lift members 12 shown in FIG. 2 of U.S. Pat. No. 5,132,942. These modifications are intended to facilitate the dedicated use of the transducer 10 in a liquid environment (i.e., by preventing the entry of water into the transducer 10), with the water-tight electrical connector 14 providing increased safety and the eye-bolt 16 making more easy the removal of the transducer 10 from the container 12. (While a modified Cassone Transducer as described herein is preferred for the transducer 10, any transducer capable of operating in a liquid environment and of generating acoustic waves at frequencies within the ranges described below would suffice.)

Figure 1:
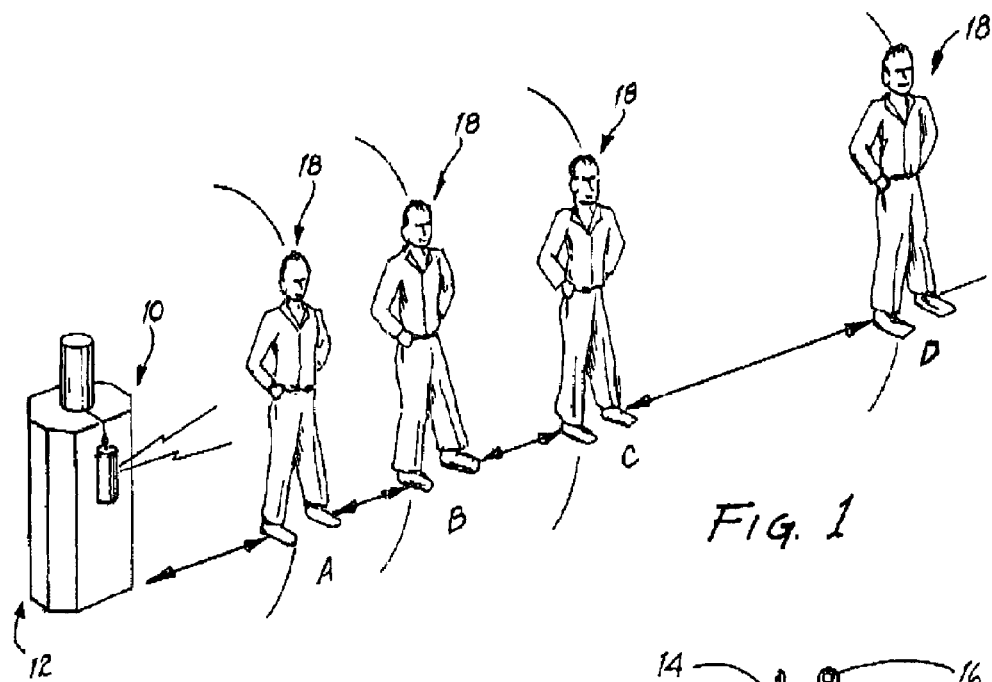
FIG. 1 is a perspective view of the practicing of the method of the present invention, with the positioning of a person at varying distances from an electroacoustic transducer.

Referring now to FIG. 1, a person 18 suffering from a medical disorder manifesting itself in the blood is positioned near the container 12 with the transducer 10 therein. (While a person 18 is shown as a human, the term "person" as used herein is intended to include animals and humans alike.) Preferably, for increased comfort during exposure, the person 18 is in a sitting position. The person 18 may be positioned at any distance relative to the transducer 10/container 12 that is determined to be therapeutically beneficial. Tests have indicated that benefit is provided within a range of from approximately one foot to approximately twenty feet—though benefit may be provided outside of this range as well as at any point within this range. Distance A is intended to represent one foot of distance, distance B represents five feet of distance, distance C represents 10 feet of distance, and distance D represents 20 feet of distance.

While FIG. 1 illustrates a person 18 positioned at different points to one side of the transducer 10, it should be noted that the transducer 10 is omni-directional, such that a person 18 could be positioned on any side of the transducer 10—or two or more persons 18 could be positioned on different sides of the transducer 10 simultaneously. Indeed, preferably, persons 18 are placed in chairs surrounding the transducer 10, and receive treatment in this relatively comfortable orientation.

The person 18 should be exposed to acoustic waves from the transducer 10 at any frequency that is determined to be therapeutically beneficial. Tests have indicated that benefit is provided within a range of from sixteen to one thousand Hertz, with particularly good results obtained between four hundred and eight hundred Hertz and optimal results obtained at approximately six hundred Hertz. The optimal wave pressure in approximately 80 decibels.

It should be noted that the acoustic waves must be audible. The presence of water (or other liquid) in the container 12 causes amplification of the audible acoustic waves issuing from the transducer 10.

The person 18 should be exposed to acoustic waves from the transducer 10 for a period of time that is determined to be therapeutically beneficial. Tests have indicated that benefit is provided by exposure for a period of time ranging from two seconds to one hour, with better results provided by exposure for a period of time ranging from fifteen minutes to forty-five minutes. A range of twenty minutes to thirty minutes is preferred, and an exposure lasting approximately twenty-five minutes appears to provide optimal results. It appears further that, for better results, the treatment should be repeated over time on a weekly or perhaps monthly basis, until the symptoms disappear permanently.

The method of the present invention has been tested on several people suffering from disorders manifesting themselves in the blood. Most of those tested experienced a significant alleviation of their symptoms. Additionally, under the auspices of the University of Nevada Las Vegas, the method of the parent applications herein has been tested. In one study, patients suffering from osteoarthritis were tested. In the other, patients suffering from peripheral vascular disease ("PVD") received treatment.

With specific regard to osteoarthritis, all of the twenty-one test participants demonstrated significant improvement both in range of motion and in pain reduction. No untoward side effects were noted. With respect to the PVD study, thirteen of the fifteen participants also benefited from the treatment, including increased blood flow and pain alleviation.

It should be noted further that good results have been achieved in certain instances by having a person 18 place the afflicted portion of his or her body in the liquid in the container 12. In one embodiment, the container 12 may be made in a jacuzzi or bath size (or may actually be a jacuzzi), with persons 18 sitting in the container 12 for treatment. When practicing such a method, it is possible for a person 18 to be positioned extremely close to the transducer 10, even less than a distance of one foot.

Although a particular embodiment of the invention has been described in detail for purposes of illustration, various modifications may be made without departing from the spirit and scope of the invention. For example, while diabetes and anemia are described as examples of disorders manifested in the blood that may be treated using the method of the present invention, it should be understood that other blood-manifested disorders are believed to be subject to beneficial treatment using the method of the present invention. Accordingly, the invention is not to be limited to any particular disorder manifested in the blood, except as by the appended claims.

I claim:

1. A method for treating medical disorders manifesting themselves in the blood comprising the steps of:
   providing a low frequency sonic transducer;
   immersing said low frequency sonic transducer in a liquid-containing container;
   positioning a person having a medical disorder manifesting itself in the blood a therapeutically beneficial distance from said container;
   wherein said therapeutically beneficial distance is between approximately one foot and approximately twenty feet from said container;
   exposing said person for a therapeutically beneficial period of time to audible acoustic waves from said low frequency sonic transducer at a therapeutically beneficial frequency;
   wherein said therapeutically beneficial frequency is between approximately sixteen and one thousand Hertz.

2. The method of claim 1 wherein said therapeutically beneficial distance is approximately one foot from said container.

3. The method of claim 1 wherein said therapeutically beneficial distance is approximately five feet from said container.

4. The method of claim 1 wherein said therapeutically beneficial distance is approximately ten feet from said container.

5. The method of claim 1 wherein said therapeutically beneficial distance is approximately twenty feet from said container.

6. The method of claim 1 wherein said therapeutically beneficial period of time is between approximately two seconds and one hour.

7. The method of claim 6 wherein said therapeutically beneficial period of time is between approximately fifteen minutes and forty-five minutes.

8. The method of claim 7 wherein said therapeutically beneficial period of time is between approximately twenty minutes and thirty minutes.

9. The method of claim 8 wherein said therapeutically beneficial period of time is approximately twenty-five minutes.

10. The method of claim 1 wherein said therapeutically beneficial frequency is between approximately four hundred and eight hundred Hertz.

11. The method of claim 10 wherein said therapeutically beneficial frequency is approximately 600 Hertz.

12. A method for treating medical disorders manifesting themselves in the blood comprising the steps of:
    providing a low frequency sonic transducer;
    immersing said low frequency sonic transducer in a liquid-containing container;
    positioning a person having at least one of diabetes and anemia between approximately one foot and approximately twenty feet from said container; and
    exposing said person for between approximately fifteen minutes and forty-five minutes to acoustic waves from said low frequency transducer at approximately six hundred Hertz.

13. A method for treating medical disorders manifesting themselves in the blood comprising the steps of:
    providing a low frequency sonic transducer;
    immersing said low frequency sonic transducer in a liquid-filled container;
    positioning at least a portion of a body of a person having at least one of diabetes and anemia a therapeutically beneficial distance from said transducer; and
    exposing said person for between approximately fifteen minutes and forty-five minutes to acoustic waves from said low frequency sonic transducer at approximately six hundred Hertz.

* * * * *